US006870185B2

(12) United States Patent
Roach et al.

(10) Patent No.: US 6,870,185 B2
(45) Date of Patent: Mar. 22, 2005

(54) INTEGRATED MICROCHIP DESIGN (75) Inventors: David John Roach, Los Gatos, CA (US); Jing Ni, Sunnyvale, CA (US); Iuliu-Ioan Blaga, Fremont, CA (US); Owe Salvén, Uppsala (SE); Stevan Bogdan Jovanovich, Livermore, CA (US)

(73) Assignee: Amersham Biosciences (SV) Corp, Sunnyvale, CA (US)

( * ) Notice: Subject to any disclaimer, the term of this patent is extended or adjusted under 35 U.S.C. 154(b) by 0 days.

(21) Appl. No.: 10/633,171

(22) Filed: Aug. 1, 2003

(65) Prior Publication Data

US 2004/0119070 A1 Jun. 24, 2004

Related U.S. Application Data (60) Provisional application No. 60/400,634, filed on Aug. 2, 2002, and provisional application No. 60/436,286, filed on Dec. 23, 2002.

(51) Int. Cl.[7] .............................................. H01L 23/58
(52) U.S. Cl. ...................................... 257/48; 257/727
(58) Field of Search ................................... 257/48, 723

(56) References Cited

U.S. PATENT DOCUMENTS 6,475,363 B1 * 11/2002 Ramsey ...................... 204/451

FOREIGN PATENT DOCUMENTS

| EP | 1 139 100 | 10/2001 | | |
|---|---|---|---|---|
| EP | 1 211 617 | 7/2002 | | |
| WO | WO01/04613 | 1/2001 | | |
| WO | WO01/70400 | 9/2001 | | |
| WO | WO02/02794 | 1/2002 | | |
| WO | 02/094440 A2 * | 11/2002 | ............ | H01I/23/58 |

OTHER PUBLICATIONS

Woolley, A., T., et al., "Functional Integration of PCR Amplifications and Capillary Electrophoresis in a Microfabricated DNA Analysis Device", Analytical Chemistry, American Chemical Society, Columbus, US vol. 68, No. 23, Dec. 1, 1996, pp. 4081–4086.

\* cited by examiner

Primary Examiner—Jasmine Clark
(74) Attorney, Agent, or Firm—Yonggang Ji; Royal N. Ronning, Jr.

(57) ABSTRACT

Structures and methods that facilitate integration and/or isolation of various functions in a microchip system are disclosed. In one embodiment, the integration of the functions is by a multi-chip, sliding linear valve approach. The chips are in continued physical contact. In a second embodiment, the chips are separated and rejoined when they are moved to the preferred position. Surface coating of the joining edges helps prevent leakage and keeps liquid in the capillary channels for both embodiments. Another embodiment relates to miniature valves. Several designs were disclosed, including the linear, edge-contact sliding valve approach. Method to fabricate very small, high aspect ratio holes in glass was also disclosed, which facilitates the above embodiments.

13 Claims, 10 Drawing Sheets

Position 1A

Position 1B

Position 1C

Position 1D

Position 2

FIG. 8

INTEGRATED MICROCHIP DESIGN

CROSS-REFERENCE TO RELATED APPLICATIONS

This application claims priority to U.S. provisional patent application Ser. No. 60/400,634 filed on Aug. 2, 2002 and claims priority to U.S. provisional patent application Ser. No. 60/436,286, filed on Dec. 23, 2002; the entire disclosures of which are incorporated herein by reference.

FIELD OF THE INVENTION

The present invention relates generally to microfluidic devices and systems and methods for using the same. More particularly, the present invention provides structures and methods that facilitate integration and/or isolation of various functions in a microchip system

BACKGROUND OF THE INVENTION

Microfluidics consist of using microchannels instead of test tubes or microplates to carry out analyses and reactions. These microchannels or microcircuits are fabricated into silicon, quartz, glass, ceramics or plastic. The size of these channels is on the order of micrometers, while the reaction volumes are on the order of nanoliters or microliters. The principle of a microfluidic device is to guide reaction media containing reagents and samples, through zones which correspond to the different steps of the protocol. The integration into a single system of reactors, sample treatment, separation, and miniature detection systems into these microfluidic systems allows the automation of complex protocols. These "laboratories on chips" have made it possible to obtain results which are efficient in terms of reaction speed, in terms of product economy and in terms of miniaturization which allows the development of portable devices. Complex protocols have been integrated and automated, including biochemical or molecular biology protocols which often require extensive manipulation. These manipulations include mixing reagents and samples, controlling the reaction temperature, carrying out thermal cycling, sample clean up, separation by electrophoresis, and detection of reaction products.

Wolley et al. (*Anal. Chem.* 68: 4081–4086 (1996)) discloses the integration of a PCR microreactor, a capillary electrophoresis system and a detector in a single device. The PCR reaction, separation of PCR products by electrophoresis, and detection of PCR products are carried out automatically. This device does not, however, integrate the mixing of reagents, and it does not allow large scale protocols to be performed.

A device or substrate allowing integration of the steps of reagent mixing and enzymatic reaction has been described by Hadd et al. (*Anal. Chem.* 69, 3407–3412, (1997)). This device provides a microcircuit of channels and reservoirs etched into a glass substrate. The moving and mixing of the fluids takes place by electrokinetics.

Microfluidic systems for the integration of protocols and of analyses have been described in international patent application WO 98/45481. One of the difficulties in implementing these devices resides in the movement of the fluids. The fluids are generally moved by electroosmosis or by electrokinetics, which requires a network of electrodes and fluid continuity. Other systems use micropumps and microvalves which are integrated in the microfluidic substrate. In the majority of cases the reactions are carried out while stationary in a microreactor and then the fluids are thus moved from one reactor to another at each step of the protocol. These systems which integrate electrodes, microvalves or micropumps are very costly and their complexity does not allow large scale applications for simultaneously treating a very large number of samples. One of the major difficulties is the distribution, mixing and transport of a very large number of products in parallel or in series.

Thus, there exists a need for devices which allow for manipulation of samples or the performance of complex protocols in which the samples are transported from one location to another using methods other than that is known in the art, and that are simple, reliable and at a low cost. There is also a need to develop a device comprising a microfluidic substrate allowing the manipulation of a large number of fluids and/or allowing a large number of complex protocols, particularly protocols involving temperature treatment, to be carried out at a low cost.

SUMMARY OF THE INVENTION

The present invention discloses structures and methods that facilitate integration and/or isolation of various functions in a microchip system. In a first embodiment, integration of the functions is achieved by a multi-chip, sliding linear valve approach. The chips are edge joined and fluidic contact is established by connection of capillary channels at the joining edges. The chips are so designed that connection of the different channels can be achieved by the sliding of the microchips against each other. Sliding can also disrupt channel connection where desired. The chips are in continued physical contact throughout the process.

In a second embodiment, the chips are separated and rejoined to establish/disrupt channel connection. The basic design of the microchip is still the same as in the first embodiment. The 'jogging' approach reduces wear at the joining edges. Specific surface coatings for the joining edges that help prevent leakage and keep liquid in the capillary channels are disclosed.

Another embodiment is related to miniature valves. Several designs are disclosed, including both linear and rotary valves in top contact with the microchip, as well as linear, edge-contact sliding valves. A method to fabricate very small, high aspect ratio holes in glass is also disclosed, which facilitates the use of the miniature, low volume valves.

DETAILED DESCRIPTION OF THE INVENTION

The present invention provides microfluidic devices and systems for integration and/or isolation of various functions in a microchip system and methods for using the same.

The present invention will now be described with regard to the accompanying drawings which assist in illustrating various features of the invention. However, it should be appreciated that the drawings do not constitute limitations on the scope of the present invention. Throughout the drawings, like numbered items represent same elements of the invention. For the sake of brevity and clarity, most figures show only one set of microfluidic channels; however, it should be appreciated that typical microfluidic devices comprise multiple sets of microfluidic channels.

In one aspect, the integration and/or isolation of the various functions in a microchip system is achieved using a sliding linear approach. According to one particular embodiment of the current invention, the integration and/or isolation of various functions in a microchip system are achieved using a three-chip system. The system consists of three micro-fabricated chips, edge joined, in fluid communication with each other. Some of the chips are moveable, by sliding action, relative to the others in order to redirect or seal the fluid paths. The three chips have polished edges that are spring biased towards each other in order to effect a low-pressure seal at the mating surfaces.

Figure 1:
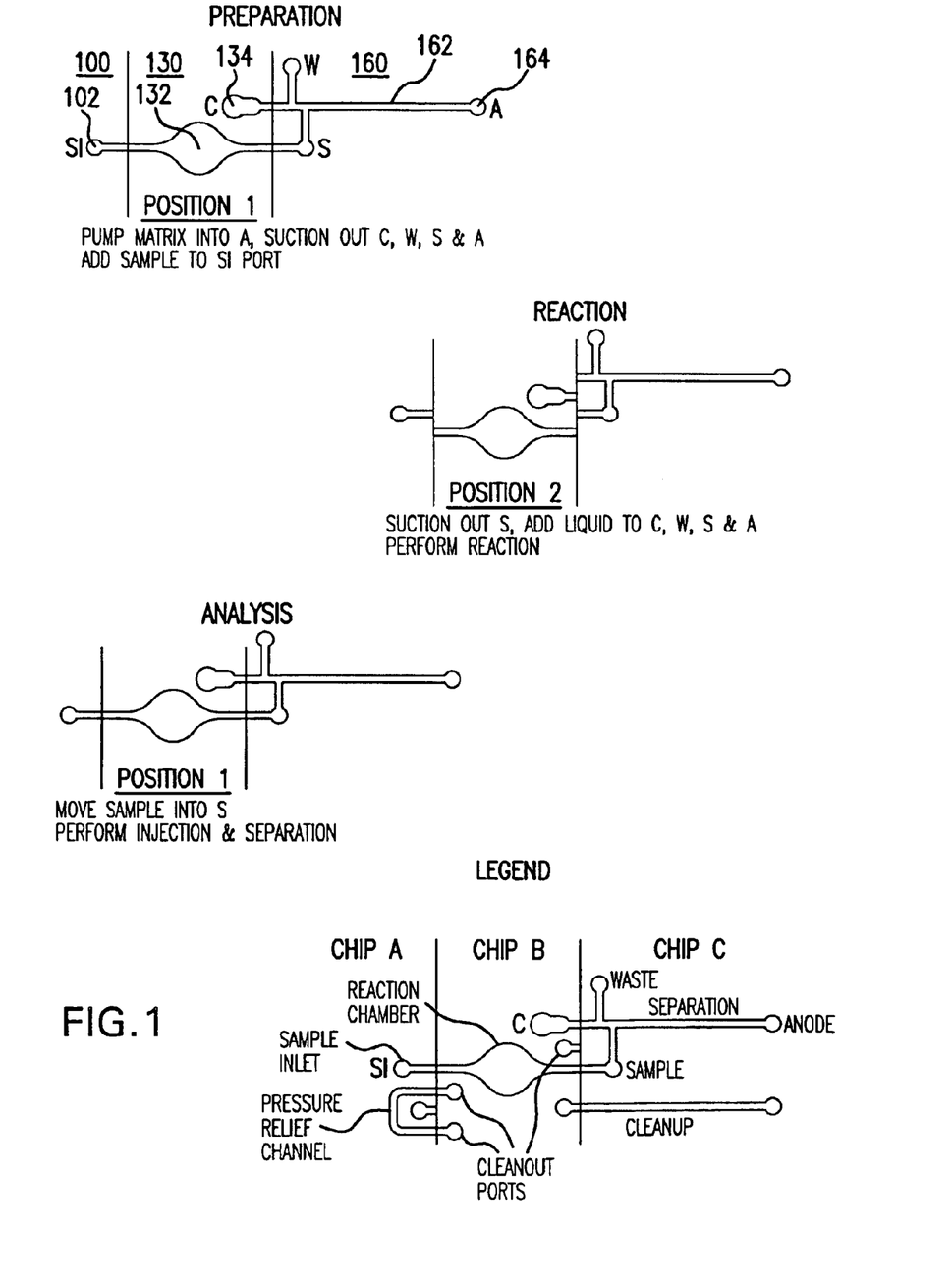
FIG. 1 shows the design and working positions of a sliding linear valve system comprising three microchips.
Figure 2:
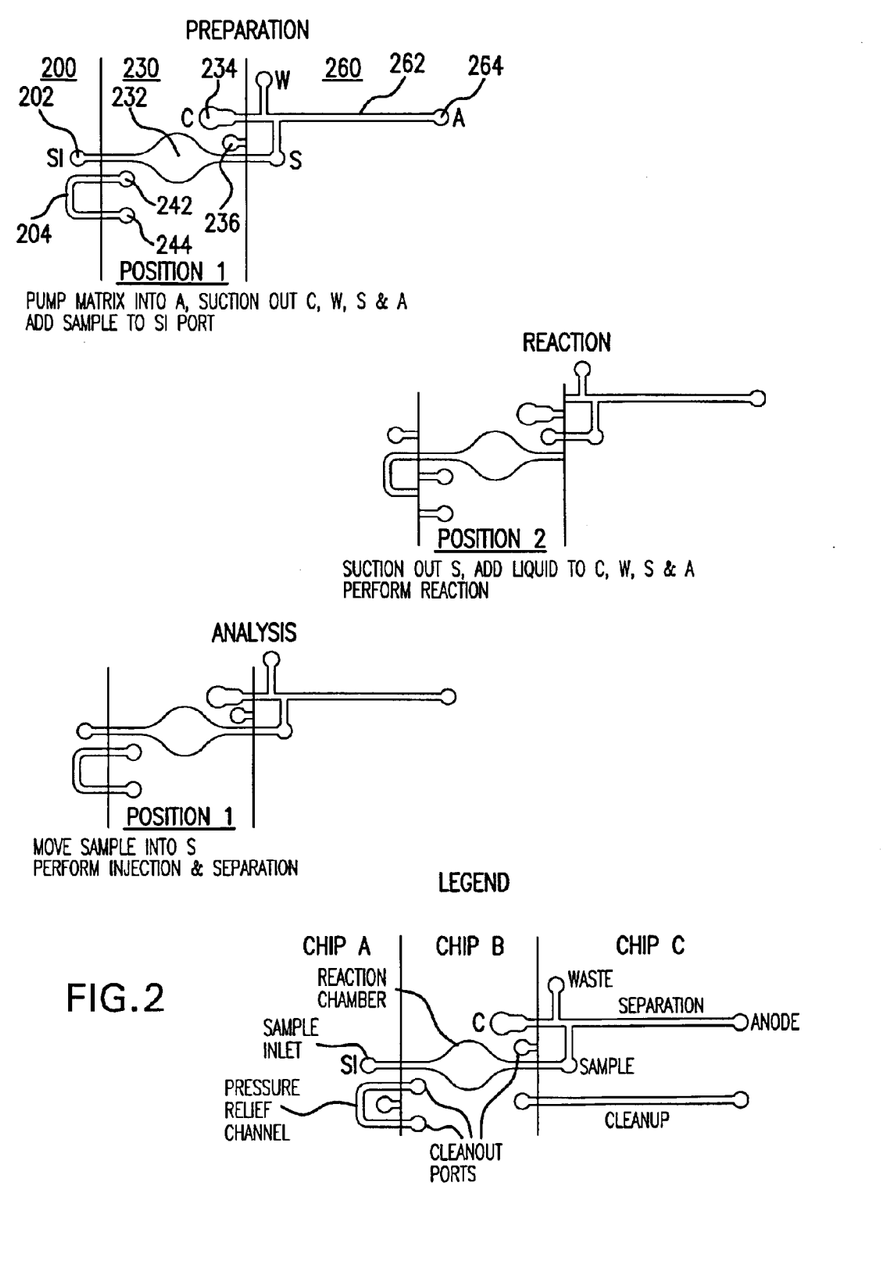
FIG. 2 shows the design and working positions of a three chip system, similar to that shown in FIG. 1 but with additional features.
Figure 3:
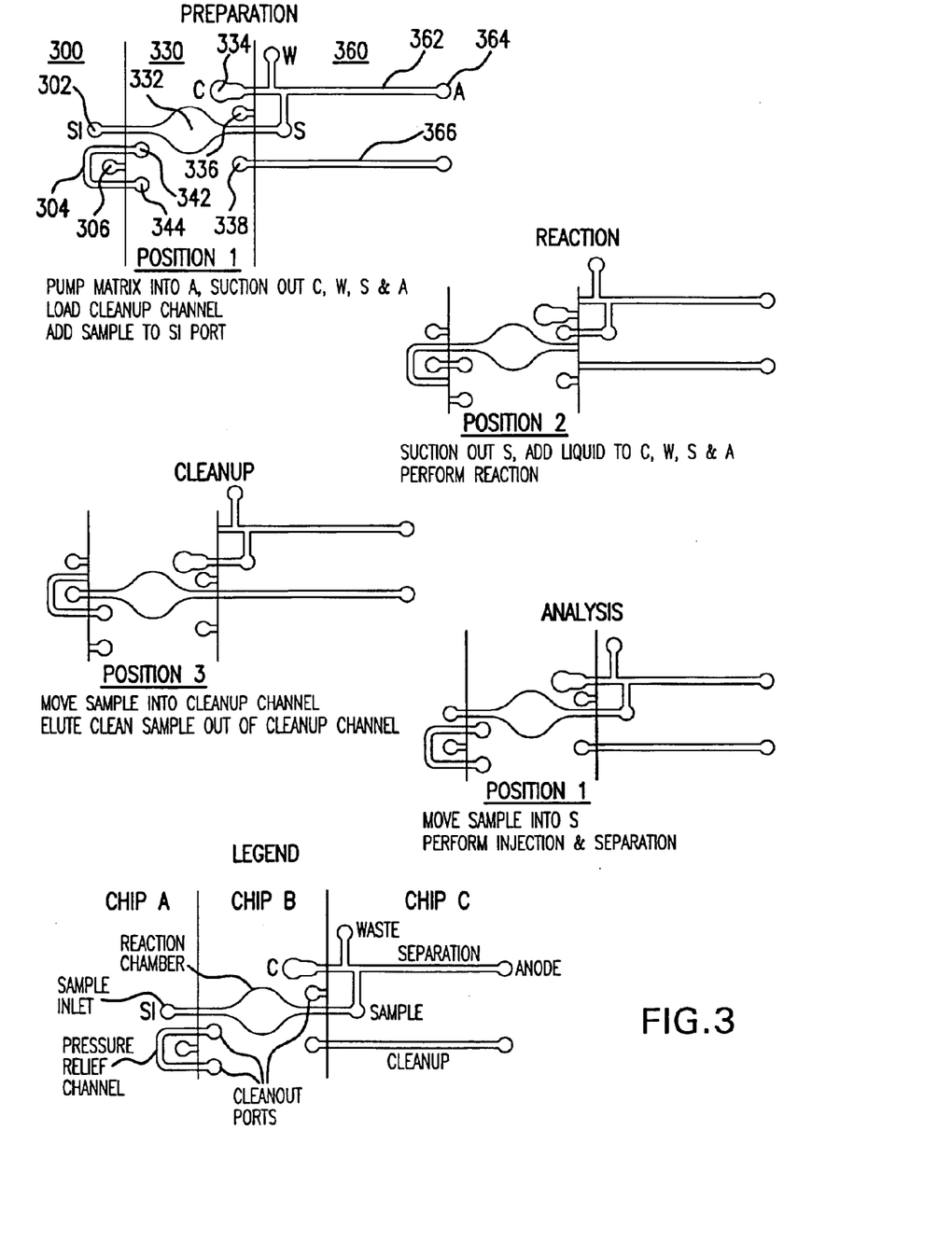
FIG. 3 shows the design and working positions of a three chip system, similar to that shown in FIG. 2 but with additional features.

In a first example of a three-chip approach (FIG. 1), a first chip (chip A, 100) contains a single sample inlet port 102. A second chip (chip B, 130) contains a reaction chamber 132 and a cathode port 134 while a third chip (chip C, 160) contains a standard separation channel 162 with a twin-tee/cross injector. In position 1 (all fluid paths connected) matrix is introduced into the anode port 164 of the third chip thereby filling the separation and injector regions. This would be followed by suction cleaning of the wells. Sample and reactants are added to the sample inlet port 102 of the first chip thereby filling the reaction chamber 132 of the second chip. The second chip is then moved to position 2 whereby the reaction chamber 132 is isolated from the rest of the device. Chemical/biological reactions are performed in the reaction chamber 132. Following the reaction process, the second chip is returned to position 1 so that the reaction products can be moved into the third chip for injection and separation. If the reaction process involves temperature changes, leakage will likely occur at the chip interfaces if the reaction chamber 132 is completely filled with fluid. To avoid this issue, either the chamber can be under filled, leaving a small air space for fluid expansion or the design can be modified to include a small channel to provide pressure relief (see FIGS. 2–3).

In the second example of a three chips approach (FIG. 2), a pressure relief channel 204 has been added, along with additional ports 236, 242, 244 to facilitate cleaning the device. The initial process of filling with matrix and sample are performed as before. Now, when the second chip (chip B, 230) is moved to position 2, the reaction chamber 232 is connected to the pressure relief channel 204 on one end and sealed on the other. The second end of the pressure relief channel is also sealed. The pressure relief channel is empty to start, and relieves the pressure built-up during reaction. Following the reaction, reaction product injection and separation are performed as in the first example above.

In the third example of a three chips approach (FIG. 3), a sample cleanup channel 366 and ports 306, 336, 338, 342, 344 are added to facilitate cleaning the device. This sample cleanup channel is either surface modified, filled with a monolithic capture matrix, or filled with media such as capture beads (wall bound or magnetic) during the first steps of matrix and sample loading. Reaction products are again created with the second chip (chip B, 330) in position 2. Next, the second chip is moved to position 3 where the reaction chamber 332 is connected to the cleanup channel 366. The contents of the reaction chamber are moved into the cleanup channel where undesired products pass on through and out of the system. The desired reaction products are then released from the capture media and moved back into the reaction chamber 332. Lastly, the second chip is returned to position 1 for sample injection and separation.

According to another embodiment of the current invention, the integration and/or isolation of various functions in a microchip system are achieved using a two chips system. The system consists of two micro-fabricated chips, edge joined, in fluid communication with each other. One of the chips is moveable, by sliding action, relative to the other chip in order to redirect or seal the fluid paths. The two chips have polished edges that are spring biased towards each other in order to effect a low-pressure seal at the mating surfaces.

Figure 4:
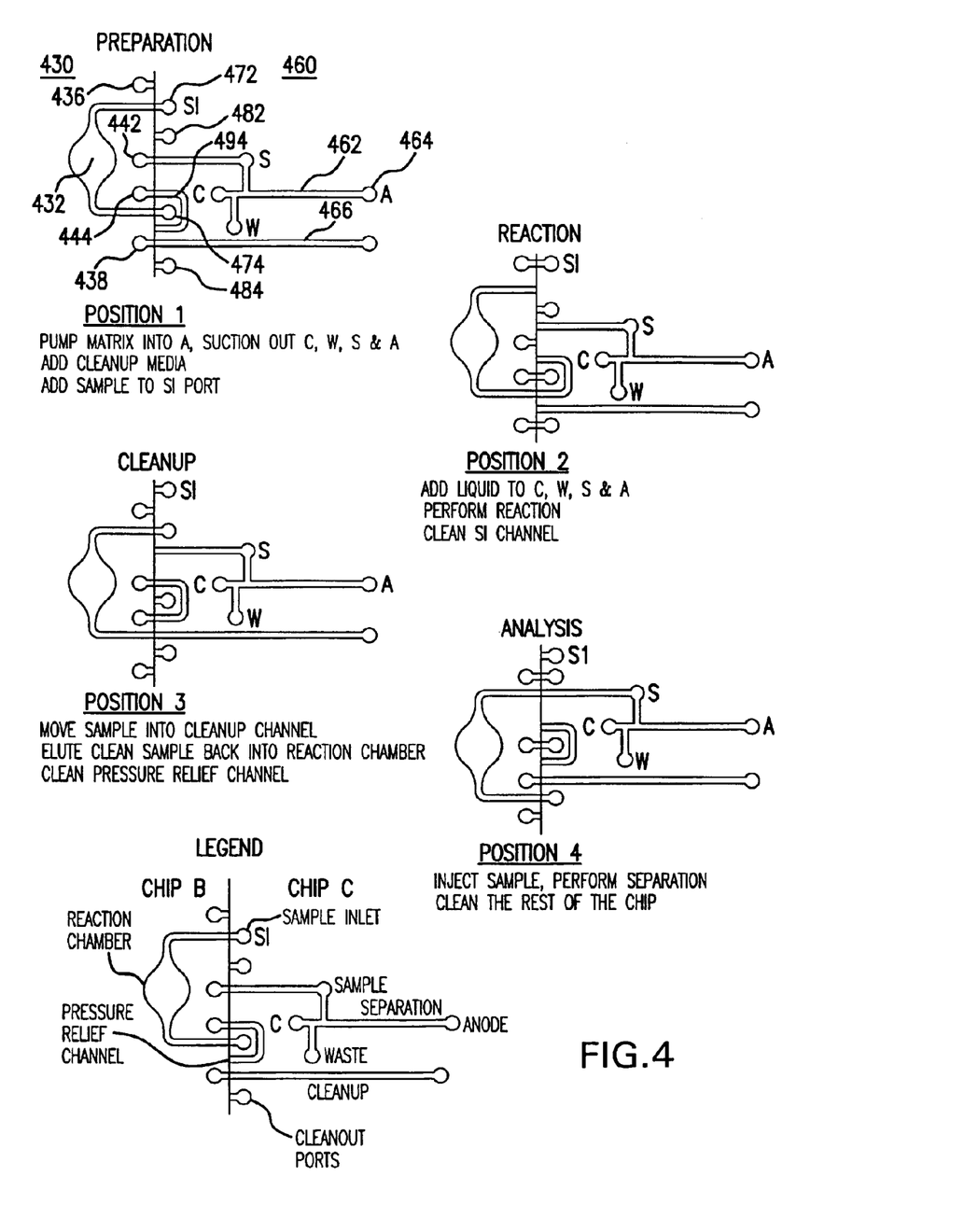
FIG. 4 shows the design and working positions of a sliding linear valve system comprising two microchips.

In an example of a two-chip approach (FIG. 4), a first chip (chip B, 430) contains a reaction chamber 432 and four small cleanout ports 436, 438, 442, 444. A second chip (chip C) contains two sample inlet ports 472, 474, a standard separation channel with a twin-tee/cross injector 462, a sample cleanup channel 466, a pressure relief channel 494, and two small cleanout ports 482, 484. In position 1, matrix is introduced into the anode port 464 of the second chip thereby filling the separation and injector regions. This would be followed by suction cleaning of the wells. Sample and reactants are added to the sample inlet port 472 or 474 of the second chip thereby filling the reaction chamber 432 of the first chip. The sample cleanup channel 466 is either surface modified, pre-filled with monolithic capture matrix, or filled with media such as capture beads (wall bound or magnetic) at this step. The first chip is then moved to position 2 whereby the reaction chamber 432 is connected to the pressure relief channel 494 on one end and sealed on the other. The second end of the pressure relief channel 494 is also sealed. Chemical/biological reactions are performed in the reaction chamber. Next, the first chip is moved to position 3 where the reaction chamber 432 is connected to the cleanup channel 466. The contents of the reaction chamber 432 are moved into the cleanup channel 466 where undesired products pass on through and out of the system. The desired reaction products are then released from the capture media and moved back into the reaction chamber 432. Lastly, the first chip is moved to position 4 for sample injection and separation.

Depending on the functions to be performed, liquids can be moved in a variety of ways including pressure, vacuum, capillary action, electrically, etc. Because connections between the chips are linear, multiple parallel structures may be micro-fabricated for increased system throughput with no additional parts count. This design does not preclude the use of glass or plastic materials, re-usable or disposable chips and in fact, one can modify the system application by changing only one of the interconnected chips. The pressure sealing requirements at the chip-to-chip interfaces are low, on the order of 5–10 psi for the viscous LPA matrix (since it is pumped in from the anode port) and even lower for low viscosity fluids like the sample.

Although a linear design has been proposed above, a number of variations are conceivable including stacked devices with either linear or rotary actuation. Alternatively, rotary valves can also be added to the top of a microchip. Multiple devices may be stacked into a 3D structure in order to increase functionality and/or parallelism. Functional structures such as those used for reacting, mixing, splitting, routing, hybridization, concentration, etc., could be incorporated. Seals or coatings may be used to increase sealing pressure or robustness. Combinations of substrate materials could also be used. For example, a glass reusable chip could be coupled to a plastic disposable or assay specific chip or maybe thermal reactions would be performed in glass chip mated to a plastic chip; the plastic would remain relatively isolated due to the low thermal conductivity property of plastic. The channel dimensions of the mating chips do not have to match, depending on the application; if large channels are mated with smaller channels, alignment tolerances are more relaxed. Devices might be fabricated in sets to make alignment even simpler. Electrodes, sensors, heaters, actuators, etc. might also be integrated. In some situations, one of the devices in a system may be disposable while the other(s) are not. Of course everything could be disposable. One could imagine preparing a sample in a system of devices and then removing one of the devices for further processing, analysis or storage.

A variation to the above sliding linear valve approach is a two-dimensional (2D) jogging approach. This approach offers a solution to make or break fluidic connections between different chips in a controlled way. In the sliding linear valve design, fluidic communication can be made or isolated between different channels on each chip by sliding one chip against the other. During the sliding process, the chips keep in contact with each other to maintain a low-pressure seal and therefore prevent leakage at the mating surfaces. Hydrophobically coating the mating surfaces of both chips is usually helpful when the chips are made of glass. The 2D jogging concept takes advantage of surface tension to create virtual valves at the edges of the chips. To isolate fluidic communication between the edge-joined chips, the two chips are pulled apart from each other. Surface tension keeps the liquid (e.g., water) within each respective channel without leaking. The chips can be moved to the next desired position, fluidic connection is re-established between the chips as soon as their edges contact. There are two major differences between the 2D jogging approach as compared to sliding. In 2D jogging, chips need not maintain contact with each other. This renders additional integration flexibility. The physical durability of the surface coating is also less of a concern in the jogging approach since no wearing occurs while the chips are moved.

Figure 5:
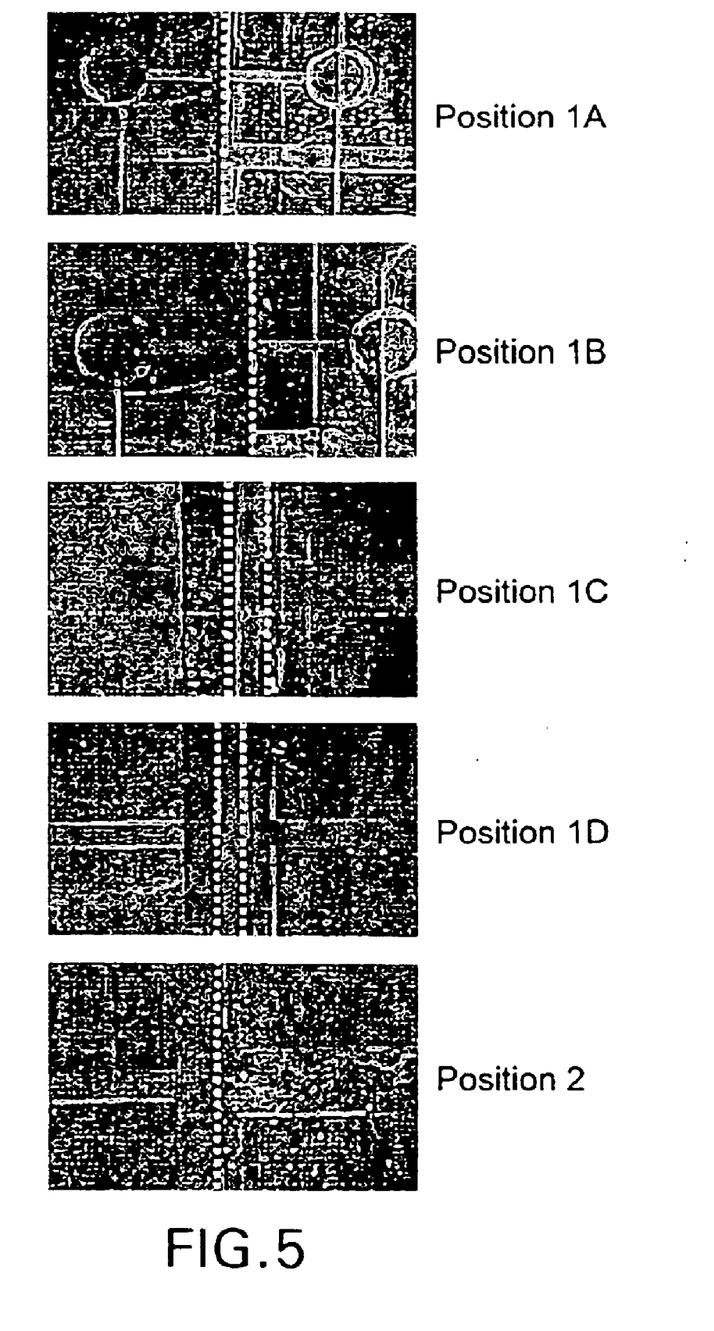
FIG. 5 shows a step-by-step example of the two dimensional jogging process for liquid transfer between microchips.

The 2D jogging approach for reactant transfer is exemplified in FIG. 5. Two chips 530 and 560 were made and edge polished. A thin layer of Cr/Au film was deposited onto the polished mating surfaces. These chips were then immersed in an ethanolic solution of octadecanethiol to form a hydrophobic monolayer coating (contact angles of greater than 90° for water were observed). The 2D jogging concept was demonstrated by transferring an aqueous dye solution between channels on different chips. FIG. 5 shows portions of the two chips, and the scales for each position are not exactly the same. The dotted lines highlight the edges of the chips, and a single dotted line at the joint of the two chips shows that the two chips are in physical edge contact to each other. On a first chip 530, a first channel 532 with a width of 270 μm is connected to a sample loading port 534. A second channel 542 is also shown on the same chip 530. On the second chip 560, a first channel 562 is connected to a sample loading port 564. A second channel 572 is also shown on the same chip 560.

In position 1A, the first and second chips were in physical contact with each other, while the first channel 532 of chip 530 was aligned with the first channel 562 of chip 560. All channels on both chips were empty. In position 1B, dye was loaded in the sample loading port 564 of the first channel 562 on the second chip 560, and then transferred to the first channel 532 on the first chip 530. The two chips were then slowly pulled apart, as shown in position 1C. Fluid connection was maintained across the short gap. As the chips were pulled further apart (position 1D of FIG. 5), fluid connection broke, and the liquid was pulled back into each respective channel by surface tension. Then the relative position of the two chips were then moved such that the first channel 532 on the first chip 530 was aligned and in physical contact with the second channel 572 on the second chip 560. The dye was then transferred into the second channel 572 on the second chip 560.

Tests on the 2D jogging approach were also successfully performed with Di water. Different coating chemistries (e.g., fluorinated monolayer, vapor deposited Teflon) can be applied to deal with organic solutions and to prevent surface adsorption of such solutions.

In another aspect, the integration and/or isolation of the various functions in a microchip system is achieved using low volume valves that are designed to be compatable with microfluidic devices. This approach also enables sealing fluidic sections during thermal cycling for example amplification, or for fluid routing and control in integrated microchips.

FIGS. 6A–6D show a variety of miniature valve designs for use with microchips. These valves consist of two major elements: a microfabricated device (a "microchip") and a small laser or conventional machined movable part. The microchip and the movable part are spring biased against each other. The microfabricated device may be made of glass or plastic and the machined part preferably out of plastic. In the first three designs (FIGS. 6A–6C), the valves are in top contact with the holes of the microchips. In the last design (FIG. 6D), the channels terminating at the edge of the microchip serve as access holes, and the valves are in end contact with the channels. In each of the designs, the movable valve component contains a small machined groove (similar or slightly larger in cross section to the microfabricated channels) that is used to connect two or more access holes in the microchip, much like the rotor in an LC valve. In the rotary designs (FIGS. 6A and 6B), the groove may connect a common hole to any of a number of radial holes or it may be configured to connect adjacent holes. With the sliding design (FIGS. 6C and 6D), one or more adjacent holes may be connected. In either configuration, one or more holes may be closed off. In practice, the moving valve(s) component may be configured as part of the instrument or as part of microchip assembly although the actuator will likely be part of the instrument. This valve approach can handle 10's of bars of pressure. We have observed 10 bar sealing.

Figure 6A:
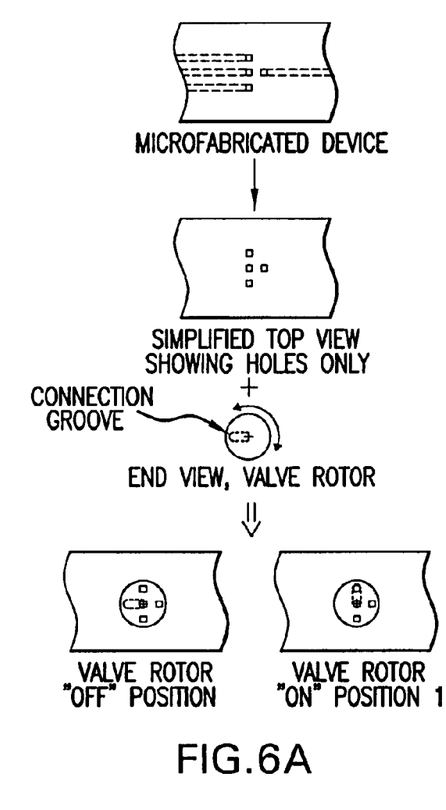
FIGS. 6A–6D show various designs of miniature valves for microchip integration.
Figure 6B:
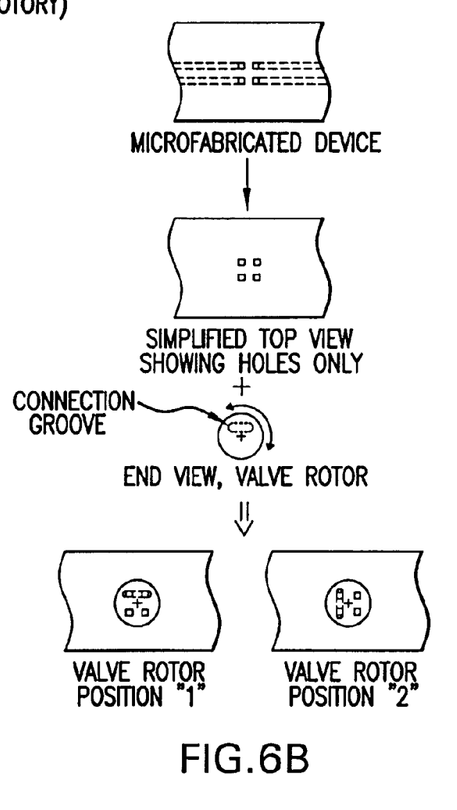
Figure 6C:
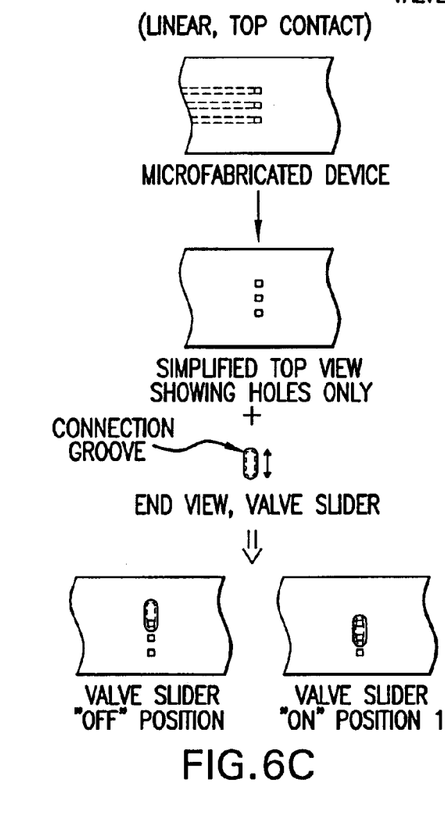
Figure 6D:
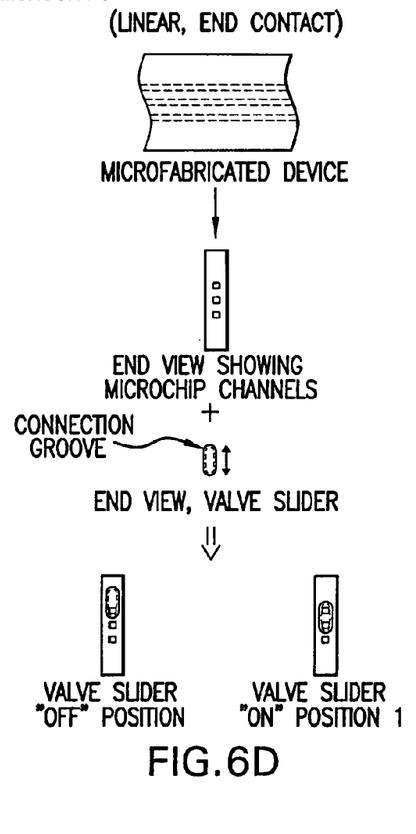
Figure 7A:
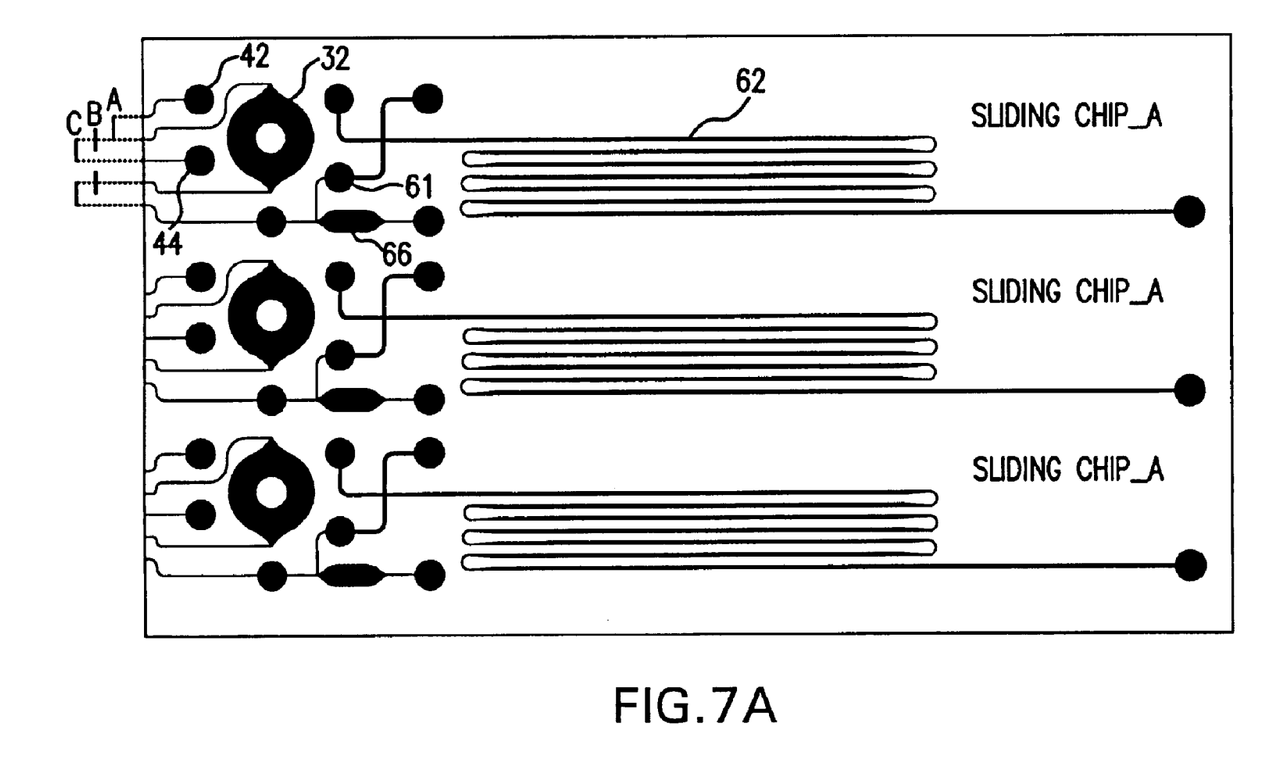
FIGS. 7A and 7B show integrated microchip designs using the edge contact, sliding linear valve approach.
Figure 7B:
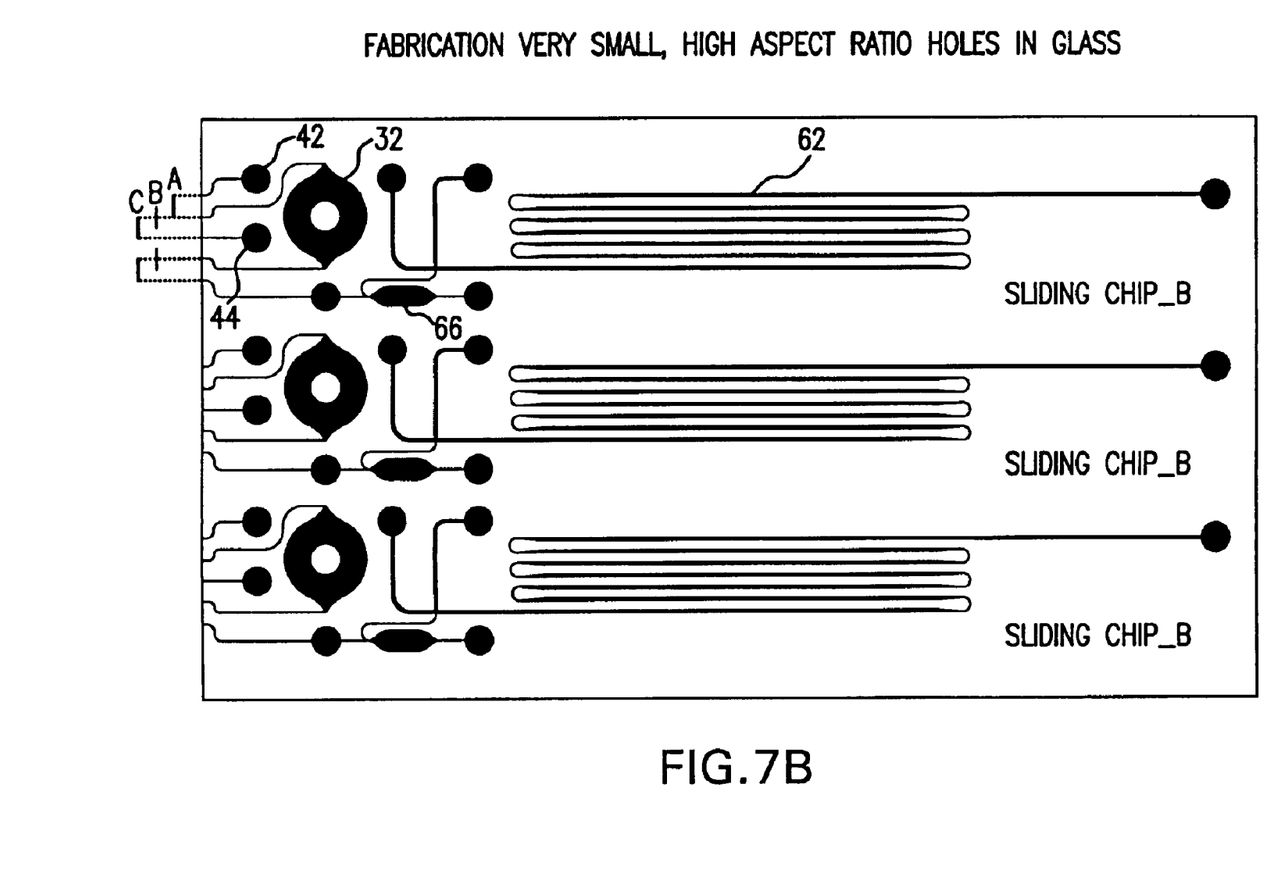

FIGS. 7A and 7B show microfabricated glass devices ("microchips") used in connection with the edge contact sliding valve as shown in FIG. 6D. Three sets of miniature systems are shown, although additional systems can be added to a microchip device. Each system contains a reaction chamber 32, a sample cleanup chamber 66, a separation channel with a twin-tee/cross injector 62, as well as two filling/cleanout ports 42 and 44. All the channels terminate at the edge of the microchip, as in the sliding linear valve designs shown in FIGS. 1–4, and serve as access holes. The sliding valves are in edge contact with the channels. The microchip and the movable part are spring biased against each other. The movable part (sliding valve) is made of plastic and contains connection grooves as shown in FIG. 6D. One or more adjacent holes may be connected (position A or C of both FIGS. 7A and 7B). And one or more holes may be closed off (position B of both FIGS. 7A and 7B). Cleaned sample is injected from the cleanup chamber directly to the separation channel in the design shown in FIG. 7B, while it is first transferred to the sample loading port 61 of the separation part, then injected in the design in FIG. 7A. DNA amplification, sample cleanup and separation were successfully carried out using these devices.

Key to the above miniature valve designs, especially those shown in FIGS. 6a-6C, are microchips with very small access holes. While it is possible to drill small holes in plastic, it is very difficult to fabricate very small, high aspect ratio holes (100 µm across×1 mm deep) in borofloat glass. Conventional diamond drilling and ultrasonic methods are limited to larger diameters and deeper holes become more difficult as dimensions shrink. Although quartz can be laser drilled, borofloat glass does not survive the process.

There is therefore a need for a novel method for fabricating glass chips incorporating very small holes with very high aspect ratios, although not arbitrarily positioned. We provide here one such process, which is especially suitable to small holes that are arranged in a linear fashion.

Figure 8:
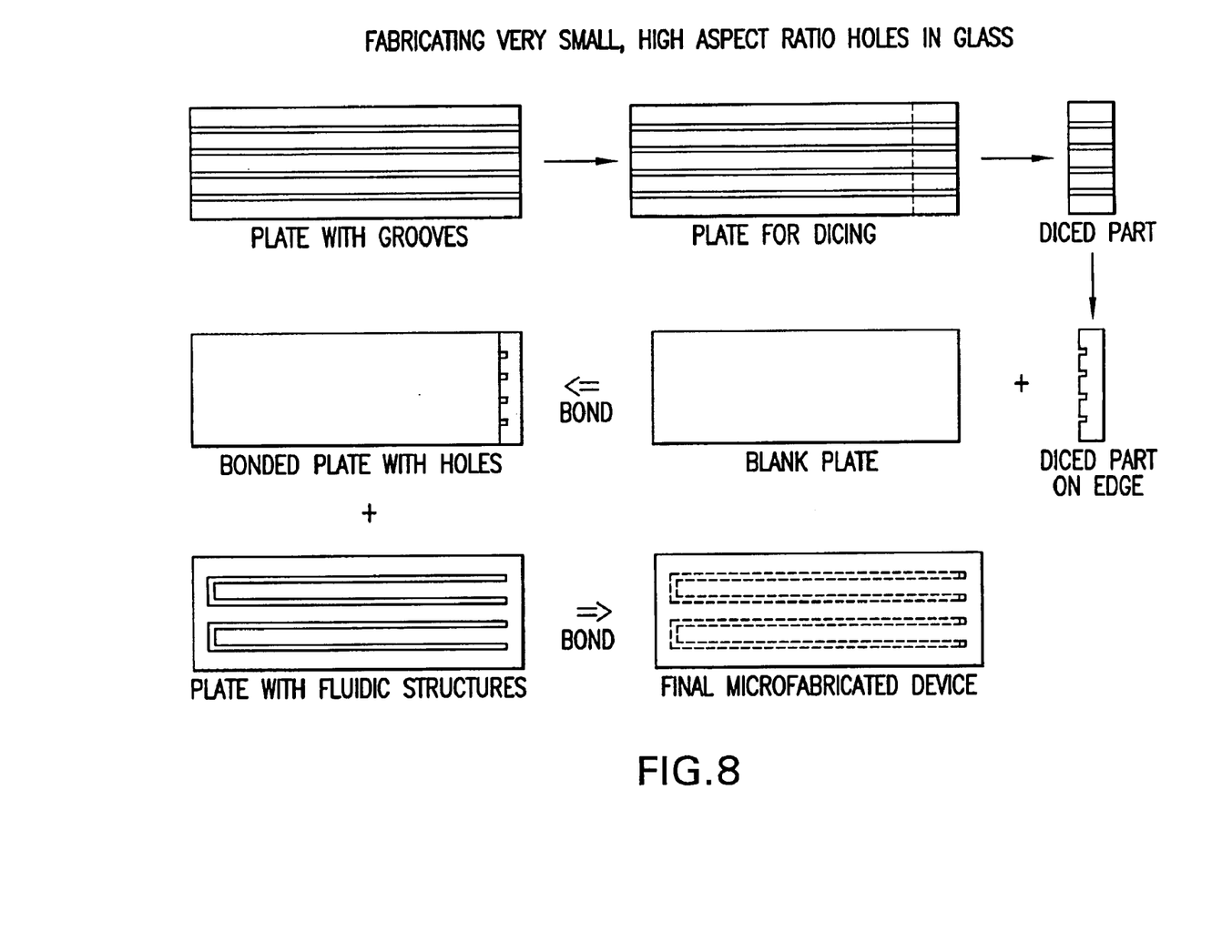
FIG. 8 shows a process for fabricating very small, high aspect ratio holes in glass.

The process consists of a number of steps, as shown in FIG. 8. First, grooves were fabricated on the surface of a glass plate. Groove fabrication can be achieved by a variety of different methods, including sawing or etching. Alternatively, glass structures with drawn internal channels can be used. Next, short strips are diced off such that the grooves (channels) are oriented perpendicular to the diced edge. Then, one (or more) of these diced strips is tipped on edge and placed groove side against the previously flattened edge of a blank glass plate. Next, these two pieces are bonded at high temperature to form an integral part and then lapped, both sides, to insure flatness. Finally, this plate is aligned and bonded to another glass plate containing fluidic structures (channels) to form a complete microfabricated device. If required, additional holes of a more conventional size may be fabricated into either of the two plates before final bonding. One might also envision fabricating grooves on both sides of the starting plate prior to dicing and then bonding to two blank plates if two columns of holes are required. Drawn structures may include multiple columns as well.

Potential applications for these devices and integration methods (sliding and jogging) should include, but are not limited to, the areas of Genomics, Proteomics, Molecular Diagnostics and cell based assays. Examples might include sample cleanup and purification, PCR, Cycle Sequencing, sample dilution, sample concentration, and isothermal, enzyme or ligand binding assays. Multiple reaction steps may be performed and samples might be prepared for detection by mass spec. In addition, applications should exist in fields outside of life sciences.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

What is claimed is:

1. An integrated microchip system, comprising:
   (i) a plurality of microchips containing capillary channels, edge joined together, and spring biased towards each other; and
   (ii) means for linearly moving said microchips against one another; wherein the capillary channels in said microchips can be connected or disconnected by the movement.

2. The integrated microchip system of claim 1, having three microchips.

3. The integrated microchip system of claim 1, having two microchips.

4. The integrated microchip system of claim 1, wherein the microchips are made of glass.

5. The integrated microchip system of claim 1, wherein any or all of the joining edges of the microchips are coated with a thin layer of Cr/Au film, and a monolayer of a hydrophobic compound.

6. The integrated microchip system of claim 1, wherein at least some of said capillary channels are filled with media solution.

7. An integrated microchip system, comprising:
   (i) a microfabricated microchip containing capillary channels;
   (ii) at least one miniature valve;
   (iii) means for connecting said at least one valve to said microchip; and
   (iv) an actuator.

8. The integrated microchip system of claim 7, wherein said at least one valve is in top contact with said microchip.

9. The integrated microchip system of claim 8, wherein said at least one valve is a rotary valve.

10. The integrated microchip system of claim 7, wherein said at least one valve is a linear sliding valve.

11. The integrated microchip system of claim 7, wherein said at least one valve is in edge contact with said microchip.

12. The integrated microchip system of claim 7, wherein said microchip is made of glass, and said at least one valve is made of plastic.

13. The integrated microchip system of claim 7, wherein at least some of said capillary channels are filled with media solution.

* * * * *